United States Patent [19]

Hamilton

[11] 3,986,566

[45] Oct. 19, 1976

[54] COMPACTION APPARATUS

[75] Inventor: Edward R. Hamilton, Austin, Tex.

[73] Assignee: Rainhart Co., Austin, Tex.

[22] Filed: May 21, 1975

[21] Appl. No.: 579,654

[52] U.S. Cl. ................................. 173/31; 173/124
[51] Int. Cl.² .......................................... B30B 9/38
[58] Field of Search ............... 173/124, 122, 53–56, 173/31; 73/84, 94, 15.6, 12; 72/453; 227/132; 404/132

[56] References Cited
UNITED STATES PATENTS

| 1,677,422 | 7/1928 | Abram | 404/133 X |
| 2,378,131 | 6/1945 | Dirksen et al. | 173/53 |
| 3,205,952 | 9/1965 | Sicotte | 173/132 X |
| 3,543,868 | 12/1970 | Drake | 173/124 X |
| 3,566,668 | 3/1971 | Browning et al. | 73/12 |

Primary Examiner—James A. Leppink
Assistant Examiner—William F. Pate, III
Attorney, Agent, or Firm—Jones, Tullar & Cooper

[57] ABSTRACT

An improved apparatus for mechanically compacting bituminous paving materials is disclosed comprising a compaction foot having a guide rod extending upwardly therefrom. A compaction hammer is slidable on the guide rod and means are provided for elevating the hammer to a position spaced above the foot. Means are provided for releasing the hammer from the elevating means, the releasing means including means for pivoting the guide rod and the hammer away from their normal vertical position to permit the hammer to fall and strike the compaction foot. The means for pivoting the guide rod includes a releaser body pivotally fixed to the guide rod.

12 Claims, 8 Drawing Figures

COMPACTION APPARATUS

FIELD OF THE INVENTION

Bituminous paving materials are generally tested for the optimum quantity of asphalt and the ideal mix design according to the widely accepted "Marshall Method" which is set forth in U.S. Pat. Nos. 2,447,586 and 2,471,227 to Bruce Marshall. In this method of testing, adopted in ASTM Designation D1159, the bituminous paving materials must first be compacted into a disk. The present invention relates, in general, to an improved apparatus for mechanically compacting bituminous paving materials in accordance with the "Marshall Method", and more particularly to compactor apparatus having an improved compactor release mechanism for reliably and accurately compacting materials for test purposes.

DESCRIPTION OF THE PRIOR ART

A number of manufacturers have marketed devices designed to mechanicaly compact bituminous materials in accordance with the "Marshall Method". One example of such a device is the Series 110 Automaic Compactor of the Rainhart Co. which has been commercially available for some time.

As seen in FIG. 1 of the drawings, these prior art compactors generally comprise a compaction foot 2 which rests on top of a specimen of bituminous materials inside a cylindrical mold (not shown). An upwardly extending guide rod 4 is attached at its lower end to the compaction foot 2, with the rod serving to guide a compaction hammer in the form of a sliding weight 6. The weight 6 includes a pair of spring-biased sliding fingers 8 which extend outwardly to engage lugs on an upwardly moving conveyor chain (not shown). The chain is effective to move the weight 6 upwardly to a release position spaced above the compaction foot 2, where a trigger 10 fixed to the guide rod 4 cams the spring-biased fingers 8 on the weight 6 away from the lugs on the conveyor chain. The weight 6 is thereby released from the chain and falls to impact on the compaction foot 2 which in turn compacts the bituminous specimen in the mold.

A number of problems are associated with such prior art mechanical compactors. The sliding weight absorbs a lot of self-destructive forces from the repetitive cycles of impacts through which it travels, and these self-destructive forces are transferred to the movable parts of the releaser mechanism, i.e., the sliding fingers, which are carried by the sliding weight. Consequently, the sliding fingers experience a high rate of mechanical failure due to fatigue.

In addition, in order to get the sliding finger and similar releaser mechanisms of the prior art compactors to work properly, it has been necessary to anchor the guide rod by applying to its upper end a heavy, lever-multiplied, weight-generated force called a surcharge weight, indicated at 12. Without such a surcharge weight, the sliding fingers aften do not release upon striking the release trigger 10, but instead lift the trigger 10 and the guide rod 4 to thereby inseat the compaction foot 1. Although the surcharge weight is generally effective to prevent unseating of the foot, it presents its own disadvantages since the added weight on the guide rod makes it more difficult to exactly comply with the requirements off the "Marshall Method" of testing which specifies a ten pound sliding weight.

Various other devices in the prior art utilize falling weights. For Example, British Pat. No. 568,752 discloses a forging mechanism having a falling weight. The weight is raised by engagement with lugs on a conveyor chain, and the weight may be released by pivoting the chain until the lugs no longer engage the weight. Similarly, U.S. Pat. No. 3,108,503 to Murek discloses a forming machine having a falling weight which is slidable on a guide rod and which may be raised by conveyor lugs. Murek's weight is released by simply allowing the lugs to rotate around the tops of the upper conveyor sprockets to a position where they normally are out of engagement with the weight. Finally, U.S. Pat. No. 3,010,665 to Smith, drawn to a rubbish compactor, discloses the same type of weight releaser as that shown in the patent to Murek.

However, none of the above-cited patents disclose or suggest the solution, as embodied in the improved releaser mechanism of the present invention, to the problems of the prior art compactor discussed earlier. Furthermore, none of the above cited patents disclose a falling weight compactor whose height of drop is independent of the specimen height, a requirement which is important in the present invention and in the "Marshall Method" of testing which requires that the weight have a constant height drop regardless of the height of the compacted specimen.

SUMMARY OF THE INVENTION

Accordingly, it is an object of the present invention to overcome the above-noted disadvantages of prior art compactors by providing a mechanical compacting apparatus having a falling compactor hammer and an improved release mechanism for the hammer.

It is a further object of the present invention to provide a compacting apparatus with an improved releaser mechanism wherein the height of drop of the compactor hammer is independent of the changing height of the specimen being compacted.

It is an additional object of the present invention to provide a compacting apparatus in which that portion of the releaser mechanism carried by the falling weight is rigid to improve the durability and fatigue resistance of the releaser mechanism.

It is another object of the present invention to provide a compacting apparatus having an improved releaser mechanism which obviates the need for a surcharge weight and, therefore, is able to more closely comply with testing specifications.

Briefly, the present invention accomplishes the foregoing and other objects by providing a compaction foot having a guide rod extending vertically upwardly therefrom adjacent a compactor frame. A compactor hammer is slidable on the guide rod and means such as a lifting lug on a conveyor chain carried by the means is provided to elevate the hammer. As the hammer reaches a desired vertical position, means for releasing it from the elevating means becomes operative. This releasing means includes a means for pivoting the guide rod away from its normal vertical position until a pair of rigid lifting fingers on the hammer no longer engages the conveyor lugs, the means for pivoting the rod being actuated by a trigger carried by the weight. The means for pivoting the rod includes a releaser body that is pivoted upwardly by the trigger around an axis fixed to the guide rod to cam the guide rod away from the compactor frame.

After the hammer has been released from the conveyor lugs, a means, specifically a spring, is operative to return the guide rod to its vertical position as the hammber is falling towards the compaction foot, to insure that the hammer is moving vertically when it strikes the foot. A new cycle of operation is initiated when the next conveyor lug engages the lifting finger on the hammer after the impact of the hammer with the foot.

BRIEF DESCRIPTION OF THE DRAWINGS

The novel features of the invention are set out with particularity in the appended claims, but the invention will be understood more fully and clearly from the following detailed description of a preferred embodiment of the invention as set forth in the accompanying drawings, in which:

DESCRIPTION OF A PREFERRED EMBODIMENT

Figure 1:
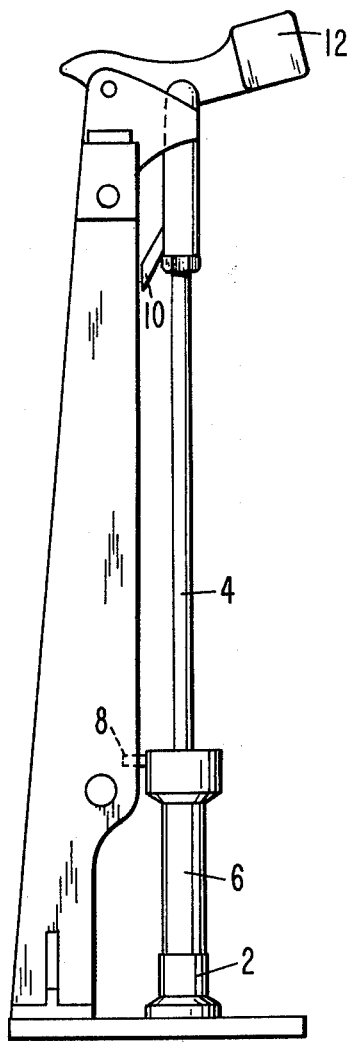
FIG. 1 is a side elevation view of a prior art compacting apparatus.
Figure 2:
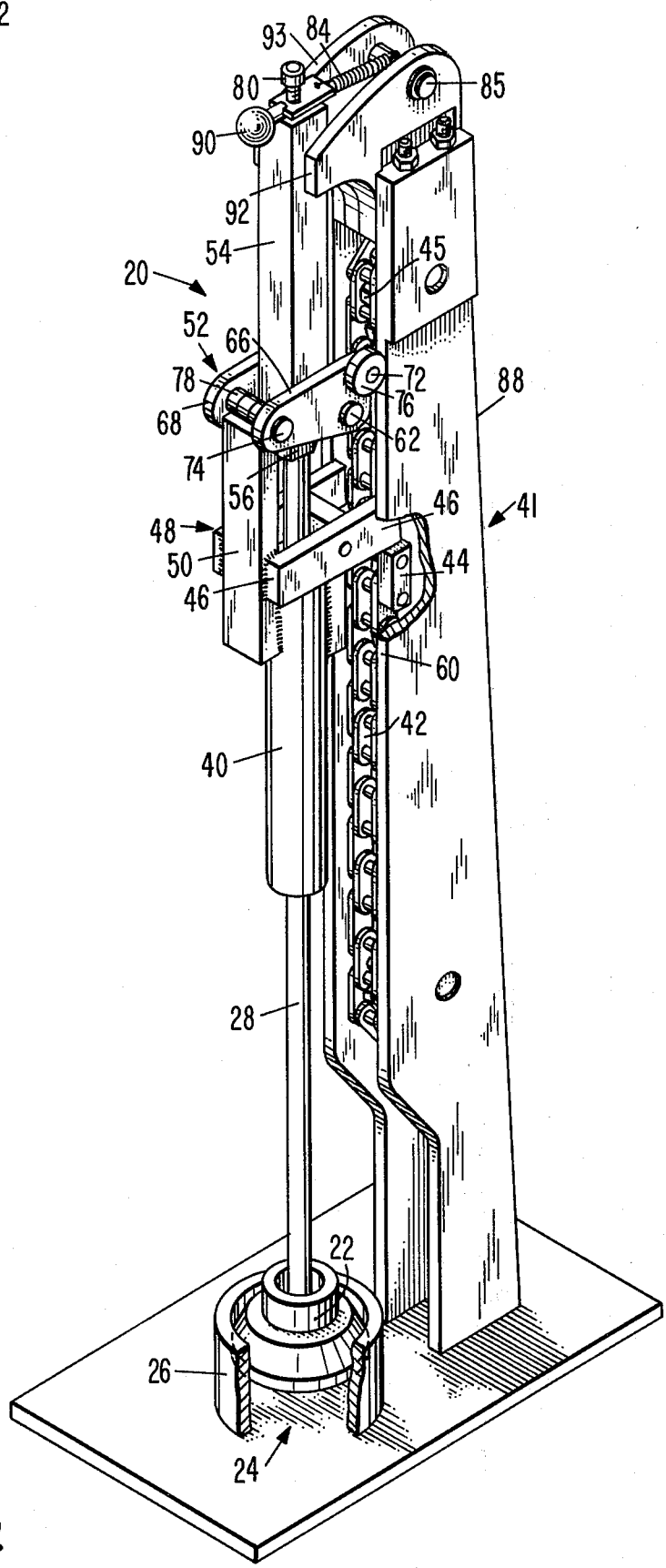
FIG. 2 is a perspective view of a preferred embodiment of the invention.

Referring now to FIG. 2 the mechanical compacting apparatus of the present invention is generally indicated at 20 and comprises a compaction foot 22 adapted to compact a specimen 24 which may be, for example, bituminous paving materials contained within a cylindrical mold assembly depicted partially broken away at 26 in FIG. 2. The mold assembly 26 is positioned on a base plate 27 of the compacting apparatus, with the foot 22 being inside the mold and contacting the upper surface of the material 24.

Figure 3:
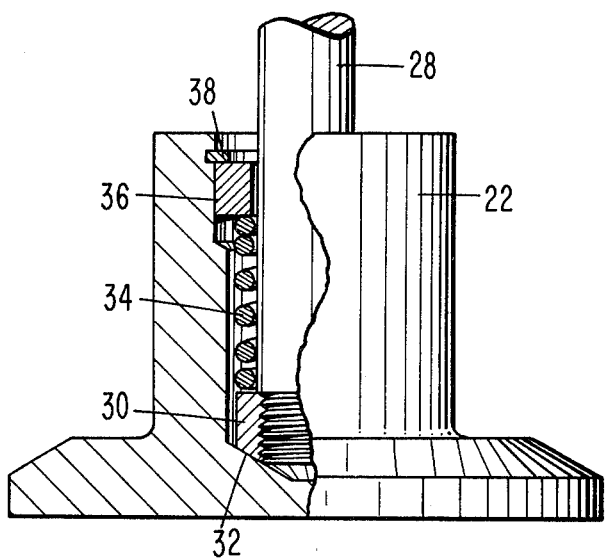
FIG. 3 is a side elevation view of the compaction foot of the preferred embodiment with parts omitted for clarity.

A guide rod 28 is attached at its lower end to the compaction foot 22 by means of an internal swivel. As seen in FIG. 3, this is accomplished by threadedly securing the lower end of rod 28 to a cone nut 30, the nut being adapted to engage the interior surface 32 of the foot 22 in a swivel-type action. The rod 28 and the nut 30 are normally held in a vertically upright position by a spring 34 located within the foot and bearing against the upper surface of nut 30 and the lower surface of an internal collar 36 which is held in place within the foot by means of a snap ring 38.

A reciprocating compaction hammer, or weight, 40 is provided for producing the compacting force on foot 22. The weight has a central bore by means of which the weight is slidably carried on the guide rod 28. Means for elevating the weight of a position spaced above the compaction foot 22 is mounted in a vertical compactor frame 41 which is secured to the base 27. The guide rod is adjacent and generally parallel to the frame and is attached thereto in a manner to be described. The elevating means preferably comprises a motor-driven conveyor chain 42 having lifting lugs 44 in the form of bars which extend transversely from the chain. The chain is mounted on upper and lower sprockets 45 and 46 which are supported in frame 41 by suitable shafts. When the rod 28 is in its normal vertical position, lifting lugs 44 are adapted to engage a pair of horizontally extending fingers 46 which are rigidly affixed to the weight 40, and which extend toward the frame 41 so that as the conveyor is driven, the lifting lugs periodically engage the fingers 46 to thereby raise the weight.

Means are provided for releasing the fingers 46 from the lifting lugs 44 at a desired vertical position of the weight to allow the weight to fall and strike the compaction foot 22. This releasing means, generally indicated at 48, comprises a vertically extending trigger 50 affixed to the top of compactor weight 40 and extending upwardly to engage and actuate a pivoting means generally indicated at 52 for pivoting the rod 28 about the compaction foot and away from its normal vertical position. The resulting pivotal motion disengages the fingers 46 of the weight 40 from the lifting lugs 44 to allow the weight to fall down the rod 28 and into contact with the top of compactor foot 22.

The means 52 for pivoting the rod comprises, as seen in FIGS. 2 and 4–8, a head piece 54 which threadedly receives the top end 55 of the guide rod 28. The position of the head piece 54 on the end of the rod 28 can be suitably adjusted by a lock nut 56 carried on the threads at the end of the rod and adapted to be tightened against the lower end of the head piece. The head piece has a flange 58 (FIG. 7) rigidly affixed thereto, the flange extending inwardly towards the inner face 60 of the frame 41. The flange 58 has a bore for a releaser pivot pin 62.

Figure 5:
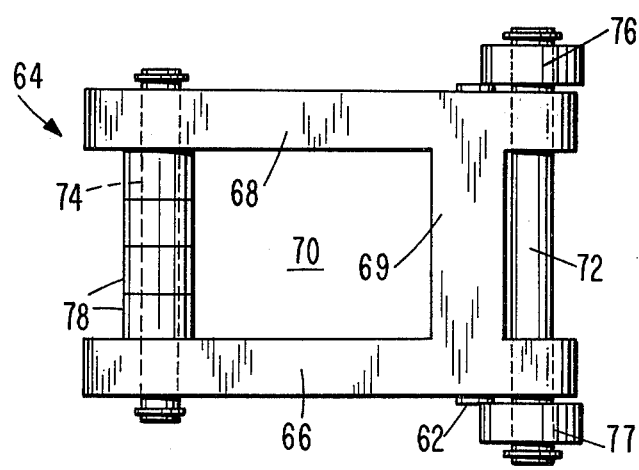
FIG. 5 is a top plan view of the releaser body of the preferred embodiment.
Figure 4:
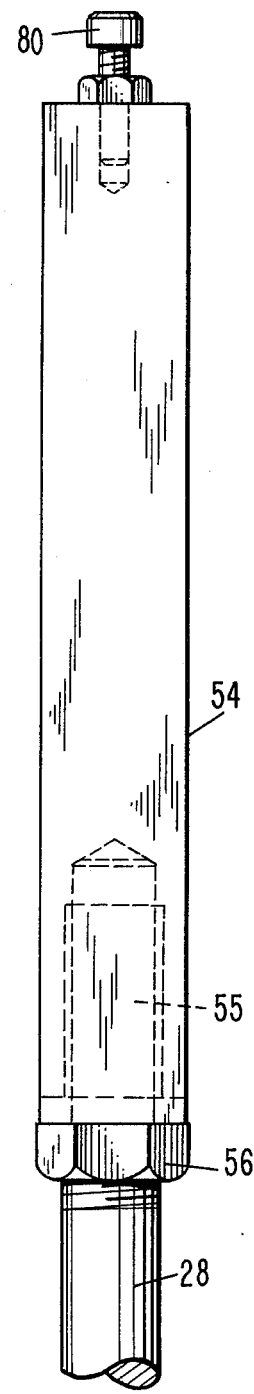
FIG. 4 is a front elevation view of the head piece of the preferred embodiment.
Figure 6:
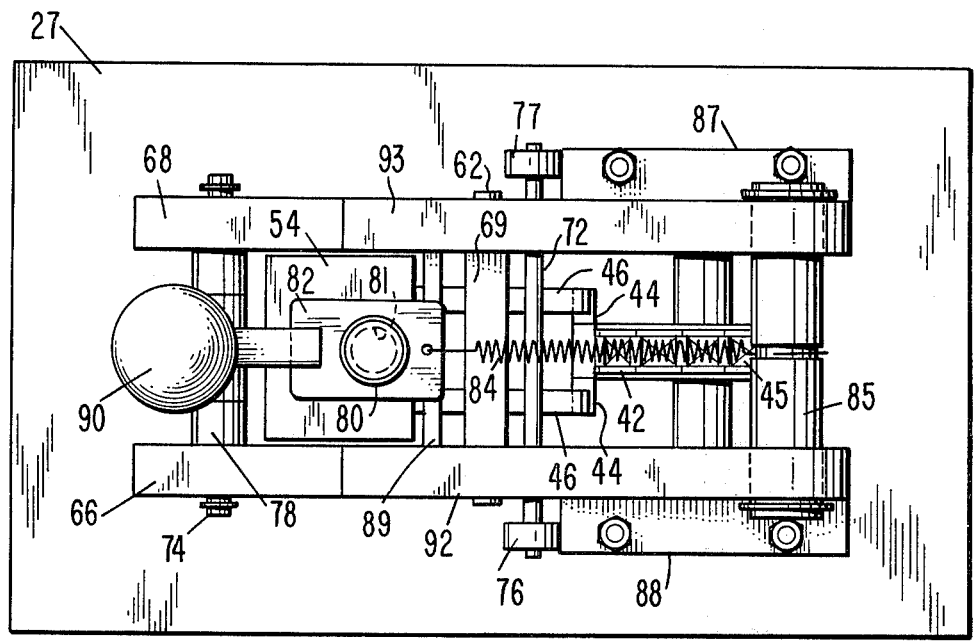
FIG. 6 is a top plan view of the compacting apparatus of the present invention.

The ends of the releaser pivot pin 62 support a releaser body, generally shown at 64, the releaser body comprising two spaced apart side walls 66 and 68 joined together by a bar or bridge 69, which define a space 70 through which the head piece 54 extends (See FIGS. 5 and 6). The walls 66 and 68 have identical shapes with the wall 66 being shown in FIGS. 7 and 8, while the bridge 69 extends between the walls above the support flange 58 to form a stop which limits the counterclockwise pivotal motion of the releaser body 64 as viewed in FIG. 7.

The walls 66 and 68 of the releaser body carry two shafts 72 and 74 as seen in FIGS. 2 and 5–8. The shaft 72 is mounted at the inner end of the releaser body and carries two ball bearings 76 and 77 outside of the walls 66 and 68, the bearings 76 and 77 being adapted to roll on the inner face 60 of frame 41. The shaft 74 is mounted at the outer end of releaser body 64 and carries a plurality of needle bearings 78 which are located between walls 66 and 68 and are adapted to be engaged by the trigger 50 mounted on the compactor weight 40. As the compactor is drawn upwardly by conveyor 42, trigger 50 strikes bearing 78 to pivot the releaser body 64 around the pivot pin 62 in a clockwise direction, as viewed in FIG. 8. The manner in which this releaser operates to disengage from the elevating means will be set forth in more detail below.

Referring again to FIGS. 2, 4 and 6, the top of the head piece 54 contains a bolt 80 which is adapted to extend through a bore 81 in a tab 82 to anchor the tab 82 to the head piece. Means are provided for returning the guide rod to its normal vertical position after the release of the weight, i.e., a return spring 84. The return spring 84 is affixed at one end to the end of the tab 82 nearest the frame 41 and at its other end to a pin 85 carried between the spaced upper ends of two flanges 92 and 93 which are integrally connected to the side walls 87 and 88 of the frame 41 of the device. The tension of spring 84 keeps the rod 28 in a normal upright position by urging the head piece 54 into engagement with a stop bar 89 secured between the flanges 92 and 93. The other end of the tab 82 carries a spherical handle element 90 which permits manual release of the compactor weight 40. The head piece 54 is received between the two forwardly extending spaced apart flanges 92 and 93 (see FIGS. 2 and 6).

In the operation of the compacting apparatus of the present invention, the rod 28 and the head piece 54 are suitably positioned with respect to frame 41, the head piece 54 being held between the flanges 92 and 93 of the frame by means of the return spring 84. The compaction foot 22 rests on top of the specimen 24 inside the mold 26 so that the rod is substantially vertical and is sufficiently close to the frame 41 that the lifting fingers 46 extend between the side walls of the frame suffciently far to engage the lugs 44. The conveyor chain 42 is driven by a suitable drive motor (not shown) in a clockwise direction as shown in FIG. 7 so that the lifting lugs 44 engage the fingers 46 to raise the weight 40.

Figure 7:
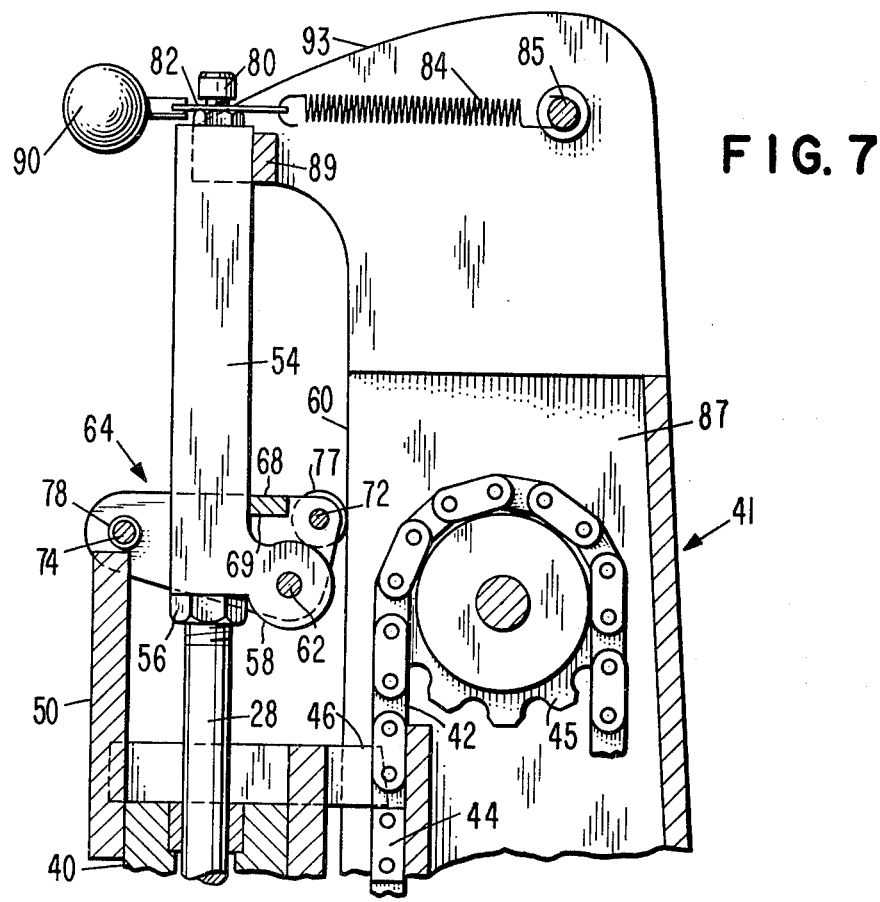
FIGS. 7 and 8 are sectional views showing the operation of the preferred embodiment.
Figure 8:
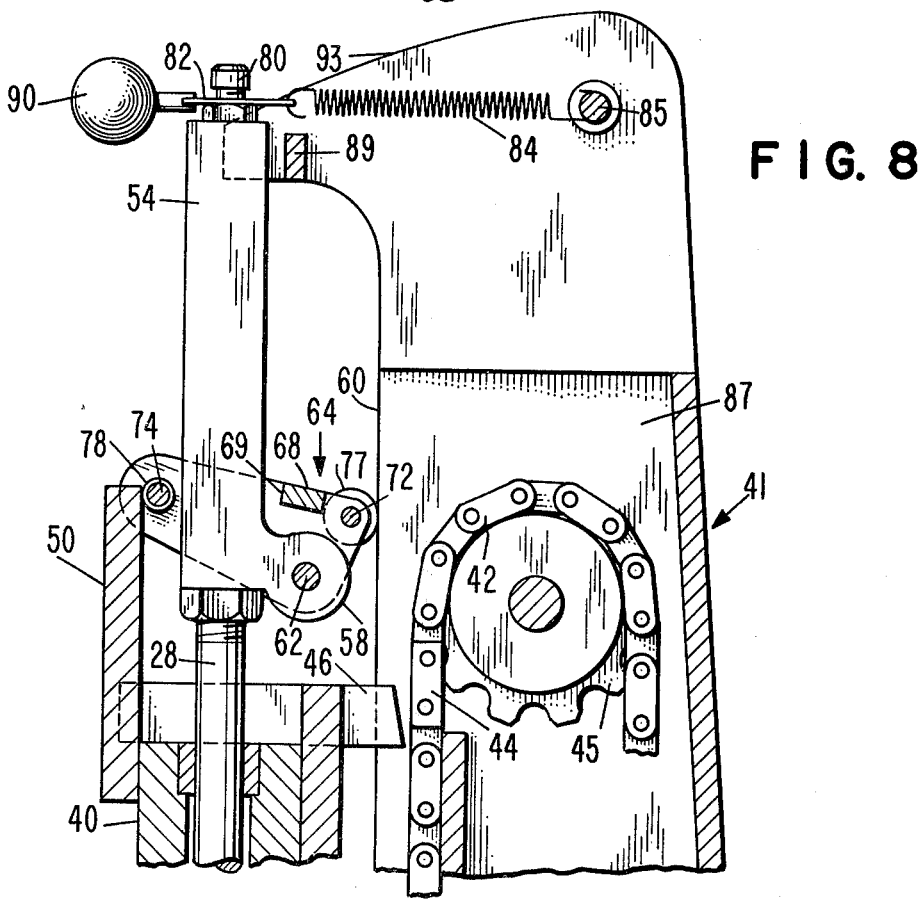

Referring now to FIGS. 2, 7 and 8, as the weight 40 moves upwardly and approaches the desired release position, the trigger 50 will engage the needle bearings 78 on the weight release mechanism 52. As the trigger continues upwardly, it will pivot the releaser body 64 around the pin 62 by virtue of its lifting engagement with the needle bearings as shown in FIG. 8. This pivoting action of the releaser body 64 cams the pin 62 and the guide rod 28 outwardly due to the rolling action of the ball bearings 76 on the face 60 of the frame. The camming action continues until the fingers 46 on the weight 40 are disengaged from the lifting lugs 44 and the weight 40 is released to fall down the rod 28 towards the compaction foot 22. As the weight 40 falls, the return spring 84 brings the guide rod 28 back to its normal vertical position so that the weight 40 will squarely strike the foot. After the impact of the weight 40 on the foot 22, the weight will be at rest until it is again raised by the next lifting lugs for another cycle of operation.

As the compaction process continues, the material specimen 24 will progressively be compacted into a more dense form. However, the guide rod 28 and the foot 22 will remain seated due to the force of gravity on top of the material 24 since the head piece 54 attached to the rod 28 is free for limited vertical movement between the flanges 92 and 93. Although the guide rod thus settles somewhat during the compaction process, the weight 40 maintains a constant height drop because the releasing means 48 is also carried by the guide rod and settles with the rod so that the distance between the top of the foot 22 and the releasing means 48 is always constant.

The present invention also provides for adjusting the height of the drop by changing the distance between the releasing means 48 and the foot 22 through an adjustment of the lock nut 56. However, once this drop height has been suitably calibrated, it will remain constant, as noted above, regardless of the degree of compaction of the material specimen. Thus, the present invention easily complies with the requirements of ASTM Designation D1159 which requires a constant height drop. In addition, the use of the needle bearings 78 on the shaft 74 minimizes overtravel drag in case the trigger 50 overruns the shaft 74 during its upward movement.

Although the present invention has been illustrated in terms of a preferred embodiment, it will be obvious to one of ordinary skill in the art that numerous modifications may be made without departing from the true spirit and scope of the invention and therefore that the scope of the invention is to be limited only by the appended claims.

I claim:

1. An apparatus for compacting materials comprising:
 a compaction foot;
 a guide rod pivotably attached at a first end to said foot and extending substantially vertically upwardly from said foot;
 a weight slidably carried on said guide rod;
 means for elevating said weight; and,
 means for releasing said weight from said elevating means, said releasing means including means for pivoting said rod away from the vertical.

2. The apparatus of claim 1 wherein the releasing means further includes a trigger affixed to said weight thereby said trigger actuates said pivoting means.

3. The apparatus of claim 2 wherein said pivoting means includes a releaser body pivotally carried by said guide rod.

4. The apparatus of claim 2 wherein said pivoting means includes a releaser body; a pin; a flange rigidly fixed to said guide rod, said flange being adapted to carry said pin; said releaser body being journalled for pivoting movement on said pin.

5. The apparatus of claim 1 including a compaction frame having a vertical column, said column being parallel to said guide rod when said rod is in its normal vertical position.

6. The apparatus of claim 5 wherein said pivoting means includes a releaser body; a pin; a flange rigidly fixed to said guide rod, said flange being adapted to carry said pin; said releaser body being journalled for pivoting movement on said pin.

7. The apparatus of claim 6 including a first shaft carried by said releaser body; a plurality of ball bearing journalled on said first shaft, said ball bearings being adapted to engage said column and to roll thereon.

8. The apparatus of claim 7 wherein said releasing means further includes a trigger affixed to said weight whereby said trigger actuates said pivoting means.

9. The apparatus of claim 8 including a second shaft carried by said releaser body, a plurality of needle bearings journalled on said second shaft; said needle bearings being adapted to be engaged by said trigger.

10. The apparatus of claim 9 wherein said elevating means includes a conveyor chain; lifting lugs affixed to said chain; and fingers rigidly attached to said weight, said fingers being adapted to engage said lugs.

11. The apparatus of claim 10 further including means for returning said rod to its normal vertical position upon release of said weight.

12. The apparatus of claim 11 wherein said returning means includes a spring, said spring affixed at one end thereof to said frame and at its other end thereof to said rod.

* * * * *

UNITED STATES PATENT AND TRADEMARK OFFICE
CERTIFICATE OF CORRECTION

PATENT NO. : 3,986,566
DATED : October 19, 1976
INVENTOR(S) : Edward R. Hamilton It is certified that error appears in the above—identified patent and that said Letters Patent are hereby corrected as shown below:

Claim 2, line 3, "thereby" should be --whereby--.

Claim 7, line 2, "bearing" should be --bearings--.

Signed and Sealed this

Twenty-eighth Day of December 1976

[SEAL]

Attest:

RUTH C. MASON
*Attesting Officer*

C. MARSHALL DANN
*Commissioner of Patents and Trademarks*